United States Patent [19]

Naumann et al.

[11] Patent Number: 5,455,371

[45] Date of Patent: Oct. 3, 1995

[54] METHOD OF PRODUCING DIFLUOROMETHYL ETHERS AND ESTERS AND ETHERS AND ESTERS PRODUCED THEREBY

[75] Inventors: Dieter Naumann, Dortmund; Wieland Tyrra, Erftstadt-Liblar; Regina Moeckel, Cologne, all of Germany

[73] Assignee: Solvay Fluor und Derivative GmbH, Hanover, Germany

[21] Appl. No.: 76,898

[22] Filed: Jun. 15, 1993

[30] Foreign Application Priority Data

Jun. 17, 1992 [DE] Germany ............ 42 19 811.9

[51] Int. Cl.⁶ .................. C07C 69/76; C07C 43/00
[52] U.S. Cl. .................. 560/111; 560/227; 560/266; 568/677; 568/684
[58] Field of Search .................. 568/677, 684; 560/111, 227, 266

[56] References Cited

U.S. PATENT DOCUMENTS 4,922,041  5/1990  Naumann et al. .

FOREIGN PATENT DOCUMENTS 0352034  1/1990  European Pat. Off. .
0388114  9/1990  European Pat. Off. .

OTHER PUBLICATIONS

*Chemical Abstracts*, 103:(19) 160622c (1985).
*Chemical Abstracts*, 110:(13) 114999c (1985).
Chen et al., *J. Fluorine Chem.*, 44:433–40 (1989).
Lange et al., *J. Fluorine Chem.*, 26:1–18 (1984).
Boit, *Beilsteins Handbuch der organischen Chemie*, vol. 6/2', p. 611 (1978).
Hine et al., J. Am. Chem. Soc. 79:5493–96 (1957).
Mitsch et al., J. Heterocyclic Chem. 2:152–56 (1965).
Bagnall et al. J. Fluorine Chem. 13:123–40 (1979).
Naumann et al., J. Organomet. Chem. 334:323–28 (1987).
Chen et al., J. Org. Chem. 54:3023–27 (1989).
Langlois, Tet. Lett. 32:3691–94 (1991).

*Primary Examiner*—Johann Richter
*Assistant Examiner*—Kimberly J. Kestler
*Attorney, Agent, or Firm*—Evenson, McKeown, Edwards & Lenahan

[57] ABSTRACT

A process for producing difluoromethyl ethers and esters by reacting an ether or an acid with a cadmium, zinc or bismuth compound containing the $CF_3$ group and selected from the group consisting of $Cd(CF_3)_2$, $Zn(CF_3)_2$, $Bi(CF_3)_3$, $CdHal(CF_3)$, $ZnHal(CF_3)$, $BiHal(CF_3)_2$ and $BiHal_2(CF_3)$ in the presence of a Lewis acid.

18 Claims, No Drawings

METHOD OF PRODUCING DIFLUOROMETHYL ETHERS AND ESTERS AND ETHERS AND ESTERS PRODUCED THEREBY

BACKGROUND OF THE INVENTION

This invention relates to a process for producing ether and ester compounds which have a difluoromethyl group, and also to novel ether compounds containing a difluoromethyl group which are obtainable according to the process of the invention.

Ether and ester compounds which have a difluoromethyl group ($CF_2H$—), can be used in combination with surface-active compounds, e.g. phosphoric acid esters, for removing water from surfaces of objects. In combination with agents which have a lubricating effect, they can be used as lubricants. Furthermore, difluoromethyl ethers, e.g. $CHF_2OC_6H_5$, $CHF_2OCH_2CF_3$, $CH_3CH_2OCF_2H$ or $CH_3OCF_2H$, can be used as substitutes for fluorochlorohydrocarbons.

Difluoromethyl esters are intermediate products and can be used as solvents.

The production by fluorination of corresponding dichloromethyl ethers is very difficult due to the low reactivity of these compounds with respect to chlorine/fluorine exchange (in which a bond breakage may also take place on the oxygen atom).

The production of difluoromethyl phenyl ethers from chloroform, potassium fluoride and phenol, which is described by B. R. Langlois in *Tetrahedron Letters* 32 (1991), pages 3691–3694, is successful, but only with a low yield.

The production of difluoromethyl ethers, e.g. from enfluorane or isofluorane, takes place by reacting the unstable starting compound fluorosulphonyl difluoroacetate and alcohols, see Chen and Wu., *J. Fluorine Chem.* 44 (1989), pages 433 to 440. The authors mention that it is also possible to produce difluoromethyl ethers from difluoroaziridine and alcohol in glass ampoules. Due to the difficulty of supplying aziridine, the application of this method is limited.

SUMMARY OF THE INVENTION

It is the object of the present invention to provide a useful process for producing difluoromethyl ethers and esters.

It is also an object of the invention to provide new difluoromethyl ethers and esters.

These and other objects of the invention are achieved by providing a process for producing a compound corresponding to the formula (I)

$$HF_2C—O—R \quad (I) \qquad (I)$$

wherein

R represents $R^1$, $R^1C(O)$, or ($R^1$—$R^2$—X);

$R^1$ represents linear or branched alkyl with 1 to 20 carbon atoms; linear or branched alkyl with 1 to 20 carbon atoms substituted by alkoxy, substituted alkoxy, halogen, CN or $NO_2$; aryl; or aryl substituted by halogen, CN, $NO_2$, C1 to C6 alkyl, aryl or aryl substituted by at least one aryl or C1 to C6 alkyl group which in turn may be substituted by one or more substituents selected from the group consisting of halogen, CN and $NO_2$; or $R^1$ and $R^2$ together form an alkylene chain with 2 to 20 carbon atoms, or an alkylene chain with 2 to 20 carbon atoms substituted by halogen, CN, $NO_2$, C1 to C6 alkyl or aryl, wherein said aryl and C1 to C6 alkyl substituents in turn may be substituted with one or more substituents selected from the group consisting of halogen, CN and $NO_2$, and X represents halogen, said process comprising reacting a compound corresponding to the formula (II)

$$R^2—O—R^1 \qquad (II)$$

wherein $R^1$ has the meaning given above;

$R^2$ is hydrogen; alkyl with 1 to 20 carbon atoms; or alkyl with 1 to 20 carbon atoms substituted by alkoxy, substituted alkoxy, halogen, CN, or $NO_2$; or $R^1$ and $R^2$ together form an alkylene chain as defined above;

or if an ester bearing a $CF_2H$—O group is to be produced, reacting a compound corresponding to the formula (III)

$$R^2—O—C(O)R^1 \qquad (III)$$

wherein $R^2$ is hydrogen, and $R^1$ has the above meaning, in the presence of a Lewis acid with a $CF_3$ group-containing cadmium, zinc or bismuth compound selected from the group consisting of $Cd(CF_3)_2$, $Zn(CF_3)_2$, $Bi(CF_3)_3$, $CdHal(CF_3)$, $ZnHal(CF_3)$, $BiHal(CF_3)_2$ and $BiHal_2(CF_3)$, wherein Hal is halide, which is dissolved in an organic solvent, and hydrolyzing the resulting reaction product.

In accordance with a further aspect of the invention, the objects are achieved by providing a compound corresponding to the formula $$HF_2C—(OCH_2CH_2)_n—OY$$

wherein n is 2, 3 or 4, and Y represents an alkyl group containing 1 to 4 carbon atoms, or to the formula $$HF_2C—O—CH_2CH_2Cl.$$

DETAILED DESCRIPTION OF PREFERRED EMBODIMENTS

The process according to the invention for the production of compounds of the general formula (I), $$HF_2C—O—R \qquad (I)$$

wherein

R stands for $R^1$, ($R^1$—$R^2$—X) or for $R^1C(O)$ and $R^1$ is linear or branched alkyl with 1 to 20 carbon atoms; linear or branched alkyl with 1 to 20 carbon atoms substituted by alkoxy, substituted alkoxy, halogen, CN, $NO_2$; aryl; aryl substituted by halogen, CN, $NO_2$, C1 to C6 alkyl, aryl, or aryl substituted by one or more aryl or C1 to C6 alkyl groups, these aryl or C1 to C6 alkyl groups themselves being substituted by one or more substituents selected from the group consisting of halogen, CN and $NO_2$; or $R^1$ and $R^2$ together form an alkylene chain with 2 to 20 carbon atoms; an alkylene chain with 2 to 20 carbon atoms substituted by halogen, CN, $NO_2$, C1 to C6 alkyl, aryl; or an alkylene chain with 2 to 20 carbon atoms substituted by aryl or C1 to C6 alkyl, these aryl or C1 to Cy alkyl groups themselves being substituted by one or more substituents selected from the group consisting of halogen, CN and NO$_2$, and X is halogen, in particular chloride or fluoride, in that compounds of the general formula (II)

$$R^2\text{---}O\text{---}R^1 \qquad (II)$$

wherein

R$^1$ has the meaning defined above;

R$^2$ is hydrogen, alkyl with 1 to 20 carbon atoms, alkyl with 1 to 20 carbon atoms optionally substituted by alkoxy, substituted alkoxy, halogen, CN, NO$_2$, or R$^1$ and R$^2$ together form an alkylene chain as defined above;

or, in that in order to produce esters which bear the CF$_2$H—O group, compounds of formula (III)

$$R^2\text{---}O\text{---}C(O)R^1 \qquad (III)$$

wherein R$^2$ is hydrogen and R$^1$ has the above meaning, are reacted in the presence of a Lewis acid with a cadmium, zinc or bismuth compound containing the CF$_3$ group and selected from the group consisting of Cd(CF$_3$)$_2$, Zn(CF$_3$)$_2$, Bi(CF$_3$)$_3$, CdHal(CF$_3$), ZnHal(CF$_3$), BiHal(CF$_3$)$_2$ and BiHal$_2$(CF$_3$), wherein Hal is halide, preferably bromide or chloride, which is dissolved in a complexing, aprotic organic solvent, and the resulting reaction product is hydrolyzed.

The term "alkoxy" may, for example, denote C1 to C4 alkoxy. The term "substituted alkoxy" may, for example, denote C1 to C4 alkoxy subsitituted by one or more halogen atoms, particularly by fluorine atoms.

According to one embodiment, therefore, the R$^2$ group is cleaved off. In this case, R$^2$ is preferably C1–C5-alkyl, in particular methyl, ethyl or t-butyl.

R$^1$ is preferably C1–C6-alkyl or phenyl, or C1–C6-alkyl or phenyl substituted by halogen, in particular one or more chlorine and/or fluorine atoms. For example, R$^1$ may be methyl, ethyl, phenyl, fluoromethyl, difluorochloromethyl, trifluoromethyl, 2,2,2-trifluoroethyl, pentafluorophenyl.

According to another embodiment, R$^1$ in the compounds of the general formula (I) stands for C1–C2-alkylene substituted by C1–C2-alkoxy, or for A-O-B-O-C, wherein A and B stand for C1–C2-alkylene and C stands for C1–C4-alkyl. According to this variant, R$^1$ stands in particular for oligomeric radicals CH$_2$CH$_2$—(OCH$_2$CH$_2$)$_n$—OY with n=1 to 4, e.g. CH$_2$CH$_2$—O—CH$_2$CH$_2$—OY, wherein Y stands for methyl, ethyl, propyl and butyl.

According to a further embodiment, R$^1$ and R$^2$ form an alkylene chain with 2 to 4 carbon atoms or an alkylene chain with 2 to 4 carbon atoms substituted by one or more halogen atoms, in particular chlorine and/or fluorine.

A wide variety of Lewis acids can be used. Suitable examples include halogen compounds of elements of groups III and IV of the periodic table. Halogen compounds of elements of group III, e.g. boron, aluminium, indium and gallium, in particular chlorides or fluorides, are especially suitable. Halogen compounds of boron and indium are very especially suitable. Boron trichloride, indium trichloride, boron trifluoride and adducts of boron trifluoride, in particular with nitriles, such as acetonitrile, ethers such as dimethyl ether, diethyl ether, methyl-t-butyl ether, are very highly suitable. Boric acid esters are also suitable.

The zinc, bismuth or cadmium compound is used dissolved in an organic solvent. It is present in the solvent in the form of an adduct. In addition to bromide and chloride, which are preferred, Hal may also stand for iodide.

Various methods known to persons skilled in the art may be used for producing this solution, as will be explained with reference to cadmium compounds. Zinc and bismuth compounds are treated analogously.

For example, cadmium compounds of the general formula (CF$_3$)$_2$Cd.D, wherein the symbol D represents an organic Lewis base, may be dissolved in a corresponding solution. In these compounds, the cadmium compound is already present as an adduct. Compounds of this type are known, cf. H. Lange, D. Naumann, *J. Fluor. Chem.*, 26 (1984), pages 1 to 18. In the formula, the symbol "D" represents 2 molecules of those Lewis bases which can only provide one pair of electrons for coordination, or 1 molecule of those Lewis bases which can provide two or more pairs of electrons for coordination. Examples of the former include nitriles, such as acetonitrile, cyclic amines, such as pyridine, and examples of the latter include ethers, for example oligomeric ethers, preferably of the formula CH$_3$—(OCH$_2$CH$_2$)$_n$—OCH$_3$ with n=1 to 4, such as ethylene glycol dimethyl ether ("glyme"), diethylene glycol dimethyl ether ("diglyme"), N,N,N',N'-tetramethyl ethylene diamine ("TMED"). These cadmium compounds are insensitive to oxygen and are crystalline substances which are stable at room temperature. As stated in the aforementioned literature source, they may be produced from dimethyl cadmium, diethyl cadmium, trifluoromethyl iodide and the corresponding Lewis base with subsequent evaporation of volatile compounds. The production of the required dialkyl cadmium compounds is described in "*Methoden der organischen Chemie* (Houben-Weyl), 4th edition (1973), volume XIII/2a, pages 867 and 868". The resulting crystalline trifluoromethyl cadmium compounds may then be dissolved in a complexing solvent, as already stated above. This embodiment for producing the solution is preferred.

In accordance with another embodiment, this solution of the trifluoromethyl compound can be produced by producing the trifluoromethyl cadmium compound in a solution which contains complexing solvent, and using it in situ in the process according to the invention, as described in the literature source quoted.

It will be apparent to a person skilled in the art that the complexing solvent stabilizes the trifluoromethyl cadmium compound. It is advantageous if during the reaction there is always a quantity of complexing solvent which is sufficient for stabilization in the reaction mixture. However, it is also clear to a person skilled in the art that the solvent need not consist of this complexing solvent. If desired, non-complexing, inert organic solvents which are miscible with the complexing solvent may also be present in the reaction mixture. These include, for example, halogenated hydrocarbons such as chloroform, hydrocarbons such as pentane, hexane or petroleum ether fractions, or aromatic solvents such as toluene. The content of such non-complexing solvents in the solvent mixture may be up to 100% by weight, for example between 0 and 90% by weight.

Aprotic, polar organic Lewis base compounds which may provide 1, 2 or more pairs of electrons for coordinate bonding are used as complexing solvents. Examples of these include aliphatic ethers, e.g. dialkyl ethers such as diethyl ether, cycloaliphatic ethers, for example tetrahydrofuran, oligomeric aliphatic ethers, for example the "glyme" and "diglyme" mentioned above, nitriles, for example acetonitrile, oligomeric tetraalkyl-substituted diamines or polyamines, for example tetramethyl ethylene diamine, mixed aliphatic-aromatic ethers (e.g. anisole), lactams, formamides, carboxylic acid amides, and sulfones.

If it is desired to use ether compounds as solvents, it is advantageous to use as the solvent, the ether starting compound of Formula (II) which is also used as a reactant.

The production of Zn(CF$_3$)$_2$.2D is described by H. Lange and D. Naumann in *J. Fluorine Chem.* 26 (1984), pages 435 and 444. According to this article, CF$_3$I is reacted with dialkyl zinc compounds, e.g. dimethyl zinc or diethyl zinc, in the presence of a Lewis base, e.g. glyme or diglyme, pyridine, forming Zn(CF$_3$)$_2$.2D.

The production of Bi(CF$_3$)$_3$ is described by D. Naumann and W. Tyrra in *J. Organomet. Chem.* 334 (1987), pages 323 ff.

The production of trifluoromethyl-zinc, trifluoro-methyl-cadmium and trifluoromethyl-bismuth halides is described in published European Patent Application No. EP 291,860. In this process, zinc, cadmium or bismuth in metallic form is reacted in a complexing solvent, for example acetonitrile, with CF$_3$Hal, e.g. CF$_3$Br. The reaction may be promoted by catalysts, e.g. iodine, and also by ultrasound.

The reaction of the zinc, bismuth or cadmium compound with the respective starting compound used takes place at a temperature of −78° C. to +20° C. The molar ratio of the starting compound (II) to the trifluoromethyl cadmium compound used may be in the range of about 1:1 to 20:1. It is preferably between about 2:1 and 4:1. The use of (II) as a solvent is advantageous.

Advantageously, the process is carried out by initially producing a mixture of the trifluoromethyl metal compound and the starting compound in the organic solvent and then adding the Lewis acid. The molar ratio of metal compound to Lewis acid is between about 1:1.5 and 1:5. Preferably it lies between about 1:1.5 and 1:3.

The Lewis acid, for example a boron trihalide adduct or indium halide such as indium trichloride, may be added as a solid. It is of course also possible to add a slurry or solution of the Lewis acid, for example in the solvent used.

After addition, an exothermic reaction then begins. If desired, an inert gas such as nitrogen may be passed over the reaction mixture, The reaction mixture also may be left for some time, for example up to several hours, in order to complete the reaction. Then a molar quantity of a protic compound, for example an acid, an alcohol or, advantageously, water, is added to the reaction mixture. To work up the mixture, volatile constituents may be separated by fractional distillation. In this manner, the desired difluoromethyl ether compound of formula (I) can be isolated.

Without being bound to any theory of the reaction, it is believed that the bond between the oxygen atom and one of the two organic radicals, for example R$^2$, is broken and this organic radical is finally replaced by the CF$_2$H group. If a halide is used as the Lewis acid, a corresponding halide of this cleaved-off organic radical R$^2$ forms in the reaction mixture. In contrast, if a compound of the general formula (II) in which R$^1$ and R$^2$ together form a (bridging) alkylene chain is used as the starting compound, a compound of the general formula HF$_2$C—O—R$^1$R$^2$X is produced if for example AlX$_3$, InX$_3$ or BX$_3$ with X=Cl, Br has been used as the Lewis acid.

The process of the invention is suitable for producing compounds of the general formula (I) in which R has the meaning given above. The process of the invention is particularly suitable for producing compounds of formula (I) in which R is CH$_3$, C$_2$H$_5$, CH$_2$CF$_3$, (CH$_2$)$_3$CH$_3$, (CH$_2$)$_4$Cl, C$_6$H$_5$, C$_6$F$_5$ or CH$_2$CH$_2$—O—CH$_2$CH$_2$—OCH$_3$.

The invention also relates to novel compounds, which can be used as lubricants and can be obtained according to the process of the invention, corresponding to the formula HF$_2$C—(OCH$_2$CH$_2$)$_n$—OY wherein n=2 to 4 and Y=C1–C4-alkyl, preferably for compounds of the general formula (IV), $$HF_2C—OCH_2CH_2—OCH_2CH_2—OY \quad (IV)$$

wherein Y represents methyl, ethyl, propyl or butyl. The compound HF$_2$C—O—CH$_2$CH$_2$Cl is also novel.

The compounds obtainable according to the process of the invention can be used for the purposes mentioned a the beginning of this specification for which they are usually used, e.g. as intermediate products in chemical synthesis, as lubricants, coolants etc.

The following examples serve to illustrate the invention in further detail without restricting its scope. Example 1 Production of HF$_2$C—O—(CH$_2$)$_4$Cl.

The adduct of diethylene glycol dimethyl ether and bis-trifluoromethyl cadmium, Cd(CF$_3$)$_2$ diglyme, was used as the trifluoromethyl cadmium compound. This compound was produced from trifluoromethyl iodide, diglyme and dimethyl cadmium in accordance with the method in H. Lange, D. Naumann, *J. Fluor. Chem.* 26 (1984), page 13.

7.6 g of (19.76 mmol) Cd(CF$_3$)$_2$ diglyme were dissolved in 25 ml tetrahydrofuran (THF) under an inert gas atmosphere. 2.9 g (13.11 mmol) of indium trichloride were added to the solution, which was stirred by means of a magnetic stirrer, at room temperature. An exothermic reaction began, and a white solid was precipitated. The reaction mixture was stirred for a further 24 hours, during which time the suspension became increasingly viscous. 10 g of water were then added to the reaction mixture. The reaction mixture was worked up by evaporating the solvent tetrahydrofuran and readily volatile constituents at room temperature under a high vacuum. The residue was then heated to 50° C. and subjected to fractional distillation under a high vacuum. Characterization by nuclear resonance spectroscopy and mass spectroscopy yielded the following data:

HCF$_2$O(CH$_2$)$_4$Cl:

$^1$H n.m.r.: (p.p.m)/CDCl$_3$: 6.12 (t, $^2J_{F-H}$ 75.2 Hz, HCF$_2$), 3.56 (m, CH$^2$), 1.66 (m, CH$_2$), 1.55 (m, CH$_2$), 3.50 (m, CH2).

$^{19}$F n.m.r.: (p.p.m.)/CDCl$_3$: −84.35 (d $^2J_{F-H}$ 75.2 Hz, $^{13}$C n.m.r.: (p.p.m.)/CDCl$_3$: 116.06 (t, $^1J_{F-C}$ 260.1 Hz, CF$_2$HO—), 62.35 (t $^3J_{F-C}$ 5.1 Hz CF$_2$HOCH$_2$—), 26.05 (—CH$_2$—), 29.52 (—CH$_2$—), 44.95 (—CH$_2$Cl).

m.s. (70 dV: $^{35}$Cl isotope; m/e): 158 (4.0%, M+).

CF$_2$HO(CH$_2$)$_2$OCH$_3$:

$^1$H n.m.r.: (CF$_2$HO) (p.p.m.)/CDCl$_3$: 6.20 (t $^2J_{F-H}$ 75.2 Hz).

$^{19}$F m.m.r.: (CF$_2$HO) (p.p.m.)/CDCl$_3$: −84.63 (d, $^2J_{F-H}$ 74.6 Hz).

m.s. (70 eV: m>80; m/e): 170 ( 10.1%, M+) .

Example 2:

Production of difluoromethyl-2,2,2-trifluoroethyl ether.

4.77 g of Zn(CF$_3$)Br.2CH$_3$CN (16.09 mmol), produced as described in published European Patent Application No. EP 291 860, were suspended in 40 ml CH$_2$Cl$_2$. 2 g of BF$_3$.CH$_3$CN (18.37 mmol) were added to this suspension at a temperature of −78° C. Then 2.5 ml of trifluoroethanol (34.72 mmol) were added. The reaction mixture was stirred for one hour at −78° C, then heated to −55° C. and heated to room temperature within about 3 hours. During this time, Zn(CF$_3$)Br.2CH$_3$CN was completely reacted. The reaction mixture was worked up by distillation under vacuum. The fraction obtained at 0° C. contained in addition to difluoromethyl-2,2,2-trifluoroethyl ether an additional compound, which may be bis-2,2,2-trifluoroethyl ether ($^{19}$F-NMR: δ –74.63 ppm; $^2J(^{19}F-^1H)$=8.9 Hz) (integration ratio: 1.3:1). The second fraction (0° C. to RT) contained only traces of difluoromethyl-2,2,2-trifluoroethyl ether, while presumably $CF_3CH_2OCH_2CF_3$ was present as the main product (integration ratio: 1:15).

$^{19}$F-NMR data of $CHF_2OCH_2CF_3$:
($CH_2Cl_2$, 20° C.)
δ($CF_3$) –75.36 ppm, tt
$^3J(^{19}F-^1H)$=8.3 Hz
$^5J(^{19}F-^{19}F)$=2.5 Hz
δ($CHF_2$) –86.74 ppm, dq
$^2J(^{19}F-^1H)$=72.5 Hz
$^5J(^{19}F-^{19}F)$=2.5 Hz.

Example 3

Production of difluoromethyl phenyl ether.

15.97 g of $Zn(CF_3)Br.2CH_3CN$ (53.87 mmol) were suspended in 60 ml $CH_2Cl_2$. 6 g of $BF_3.CH_3CN$ (55.12 mmol) were added to the suspension, with stirring, at –78° C. Then 10 g phenol (106.26 mmol) were added. The reaction mixture was stirred for one hour at –78° C., then heated to –55° C. and warmed to room temperature over a period of 3 hours. $Zn(CF_3)Br.2CH_3CN$ could no longer be detected by $^{19}$F-NMR spectroscopy. The reaction mixture was worked up by vacuum distillation. At 0° C., the majority of the solvent had been removed from the reaction mixture. Distillation in a stream of hot air yielded a reddish-brown colored solution which contained phenol, acetonitrile, dichloromethane, presumably $C_6H_5OCF_2OC_6H_5$ ($^{19}$F-NMR: δ –76.39 ppm, $^1J(^{19}F-^{13}C)$=290.4 Hz, Δδ0.1282 ppm) and $BF_3$ adducts in addition to difluoromethyl phenyl ether. After the addition of NaF, the mixture was freed of residual solvent in a vacuum (170–210 mbar). The mixture was worked up further by renewed distillation in a stream of hot air, which meant that a high enrichment of difluoromethyl phenyl ether was achieved.

$^{19}$F-NMR data of $CHF_2OC_6F_5$
($CDCl_3$, 20° C.)
δ($CHF_2$) –81.23 ppm, d
$^2J(^{19}F-^1H)$=73.8 Hz
$^1J(^{19}F-^{13}C)$=258.9 Hz; Δδ0.1247 ppm
$^1$H-NMR data of $CHF_2OC_6H_5$
($CDCl_3$, 20° C.)
δ($CHF_2$) 6.50 ppm, t
$^2J(^{19}F-^1H)$=74.0 Hz
δ(aromatic) 6.85; 7.12; 7.35 ppm Example 4:

Production of chlorodifluoroacetic acid difluoromethyl ester.

1.07 g of $Zn(CF_3)Br.2CH_3CN$ (3.61 mmol) were suspended in 10 ml $CH_2C_2$, and 0.4 g $BF_3.CH_3CN$ (3.67 mmol) were added thereto with stirring at –65° C. Then approximately 1.04 g of chlorodifluoroacetic acid (approximately 7.97 mmol) were added. After 30 minutes, the cold bath was removed and the mixture was heated to room temperature with stirring. The Zn compound used could no longer be detected.

$^{19}$F-NMR data of $CF_2ClCOOCF_2H$:
($CH_2Cl_2$, 20° C.)
δ($CF_2Cl$) –65.91 ppm
δ($CF_2H$) –91.74 ppm, d
$^2J(^{19}F-^1H)$=68.7 Hz.

Example 5

Production of trifluoroacetic acid difluoromethyl ester.

1.12 g of $Zn(CF_3)Br.2CH_3CN$ (3.78 mmol) were suspended in 10 ml $CH_2Cl_2$, and 0.4 g $BF_3.CH_3CN$ (3.67 mmol) were added thereto at –65° C. Then 0.7 ml of trifluoroacetic acid (9.09 mmol) were added, with stirring. After 30 minutes, the cold bath was removed, and the mixture was heated to room temperature with stirring.

$^{19}$F-NMR data of $CF_3COOCF_2H$:
($CH_2Cl_2$, 20° C.)
δ($CF_3$) –76.1 ppm
δ($CF_2H$) –91.93 ppm, d
$^2J(^{19}F-^1H)$=64.8 Hz.

Example 6

Production of pentafluorobenzoic acid difluoromethyl ester.

3 g of $Zn(CF_3)Br.2CH_3CN$ (10.12 mmol) were suspended in 20 ml $CH_2C_2$. The mixture was cooled to –60° C., and 1.1 g of $BF_3.CH_3CN$ (10.10 mmol) were added thereto with stirring. Then 4.3 g of pentafluorobenzoic acid (20.27 mmol) were added, The reaction mixture was left at this temperature for 1 hour before the cold bath was removed. It was warmed to room temperature with stirring. The $Zn(CF_3)Br.2CH_3CN$ was completely reacted.

$^{19}$F-NMR data of $C_6F_5COOCF_2H$:
($CH_2Cl_2$, 20° C.)
δ($CF_2H$) –92.54 ppm, d
$^2J(^{19}F-^1H)$=70.1 Hz
δ($C_6F_5$, o) –136.87 ppm
δ($C_6F_5$, p) –145.66 ppm
δ($C_6F_5$, m) –160.70 ppm.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A process for producing a compound corresponding to the formula (I)

$$HF_2C—O—R \qquad (I)$$

wherein

R represents $R^1$, $R^1C(O)$, or $(R^1—R^2—X)$;

$R^1$ represents linear or branched alkyl with 1 to 20 carbon atoms; linear or branched alkyl with 1 to 20 carbon atoms substituted by alkoxy, substituted alkoxy, halogen, CN or $NO_2$; aryl; or aryl substituted by halogen, CN, $NO_2$, C1 to C6 alkyl, aryl or aryl substituted by at least one aryl group or C1 to C6 alkyl group or aryl group or C1 to C6 alkyl group substituted by one or more substituents selected from the group consisting of halogen, CN and $NO_2$; or $R^1$ and $R^2$ together form an alkylene chain with 2 to 20 carbon atoms, or an alkylene chain with 2 to 20 carbon atoms substituted by halogen, CN, $NO_2$, C1 to C6 alkyl or aryl, or aryl and or C1 to C6 alkyl substituted with one or more substituents selected from the group consisting of halogen, CN and $NO_2$, and X represents halogen, said process comprising reacting a compound corresponding to the formula (II)

$$R^2-O-R^1 \quad (II)$$

wherein

R¹ has the meaning given above;

R² is hydrogen; alkyl with 1 to 20 carbon atoms; or alkyl with 1 to 20 carbon atoms substituted by alkoxy, substituted alkoxy, halogen, CN, or NO₂; or R¹ and R² together form an alkylene chain as defined above;

or if an ester bearing a CF₂H—O group is to be produced, reacting a compound corresponding to the formula (III)

$$R^2-O-C(O)R^1 \quad (III)$$

wherein

R² is hydrogen, and

R¹ has the above meaning, in the presence of a Lewis acid with a CF₃ group-containing cadmium, zinc or bismuth compound selected from the group consisting of Cd(CF₃)₂, Zn(CF₃)₂, Bi(CF₃)₃, CdHal(CF₃), ZnHal (CF₃), BiHal(CF₃)₂ and BiHal₂(CF₃), wherein Hal is halide, which is dissolved in an organic solvent, and hydrolyzing the resulting reaction product.

2. A process according to claim 1, wherein X represents chlorine or fluorine.

3. A process according to claim 1, wherein Hal represents bromide or chloride.

4. A process according to claim 1, wherein said Lewis acid comprises a halogen compound of an element of Group III of the periodic table.

5. A process according to claim 4, wherein said Lewis acid is a chloride or fluoride of an element of Group III of the periodic table.

6. A process according to claim 4, wherein said Lewis acid is a halogen compound of boron or indium.

7. A process according to claim 6, wherein said Lewis acid is selected from the group consisting of boron trifluoride, adducts of boron trifluoride with acetonitrile, dimethyl ether, diethyl ether or methyl-t-butyl ether, boron trichloride and indium trichloride.

8. A process according to claim 1, wherein said solvent is selected from the group consisting of aliphatic ethers, cycloaliphatic ethers, oligomeric aliphatic ethers, nitriles, lactams, formamides, carboxylic acid amides, sulfones, halogenated hydrocarbons, alcohols and optionally substituted aromatic hydrocarbons, 9. A process according to claim 8, wherein said solvent is an oligomeric ether corresponding to the formula $$CH_3-(OCH_2CH_2)_n-OCH_3,$$

wherein n is 1 to 4.

10. A process according to claim 1, wherein the reaction of the compound of formula (II) to form a compound of formula (I) is carried out at a temperature of −78° C. to +20° C.

11. A process according to claim 1, wherein the molar ratio of the compound of formula (II) to the zinc, bismuth or cadmium compound is between about 1:1 and 20:1.

12. A process according to claim 11, wherein the molar ratio of the compound of formula (II) to the zinc bismuth or cadmium compound is between 2:1 and 4:1.

13. A process according to claim 1, wherein the molar ratio of Lewis acid to zinc, bismuth or cadmium compound is between about 1.5:1 and 5:1.

14. A process according to claim 13, wherein the molar ratio of Lewis acid to zinc bismuth or cadmium compound is between about 1.5:1 and 3:1.

15. A process according to claim 1, wherein R² represents an alkyl group containing 1 to 5 carbon atoms.

16. A process according to claim 15, wherein R² represents a methyl, ethyl or t-butyl group.

17. A process according to claim 1, wherein R¹ represents an alkyl group containing 1 to 6 carbon atoms, and alkyl group containing 1 to 6 carbon atoms substituted by halogen, a phenyl group, or a phenyl group substituted by halogen.

18. A process according to claim 1, wherein R¹ and R² represent an alkylene chain with 2 to 4 carbon atoms or an alkylene chain with 2 to 4 carbon atoms substituted by halogen.

* * * * *